United States Patent
Bridle et al.

(10) Patent No.: US 9,821,054 B2
(45) Date of Patent: Nov. 21, 2017

(54) METHOD OF VACCINATION COMPRISING A HISTONE DEACETYLASE INHIBITOR

(75) Inventors: Byram Bridle, Guelph (CA); Brian Lichty, Brantford (CA); Yonghong Wan, Hamilton (CA); Jean-Simon Diallo, Ottawa (CA); Chantal Lemay, Ottawa (CA); John Bell, Ottawa (CA)

(73) Assignee: Turnstone Limited Partnership, Toronto (CA)

( * ) Notice: Subject to any disclaimer, the term of this patent is extended or adjusted under 35 U.S.C. 154(b) by 0 days.

(21) Appl. No.: 14/004,546

(22) PCT Filed: Mar. 9, 2012

(86) PCT No.: PCT/CA2012/000212
§ 371 (c)(1),
(2), (4) Date: Mar. 25, 2014

(87) PCT Pub. No.: WO2012/122629
PCT Pub. Date: Sep. 20, 2012

(65) Prior Publication Data
US 2014/0193458 A1    Jul. 10, 2014

Related U.S. Application Data

(60) Provisional application No. 61/451,794, filed on Mar. 11, 2011.

(51) Int. Cl.
| | | |
|---|---|---|
| *C12N 7/00* | (2006.01) | |
| *C12N 15/86* | (2006.01) | |
| *A61K 39/29* | (2006.01) | |
| *A61K 39/00* | (2006.01) | |
| *A61K 38/12* | (2006.01) | |
| *A61K 38/15* | (2006.01) | |
| *A61K 38/16* | (2006.01) | |
| *A61K 45/06* | (2006.01) | |
| *A61K 31/165* | (2006.01) | |
| *A61K 31/167* | (2006.01) | |
| *A61K 31/18* | (2006.01) | |
| *A61K 31/19* | (2006.01) | |
| *A61K 31/192* | (2006.01) | |
| *A61K 31/4045* | (2006.01) | |
| *A61K 31/4406* | (2006.01) | |
| *A61K 31/4745* | (2006.01) | |
| *A61K 31/713* | (2006.01) | |
| *A61K 31/506* | (2006.01) | |
| *A61K 39/02* | (2006.01) | |
| *A61K 39/04* | (2006.01) | |
| *A61K 39/12* | (2006.01) | |
| *A61K 39/165* | (2006.01) | |
| *A61K 39/17* | (2006.01) | |
| *A61K 39/205* | (2006.01) | |
| *A61K 39/285* | (2006.01) | |
| *A61K 35/766* | (2015.01) | |

(52) U.S. Cl.
CPC ............ *A61K 39/29* (2013.01); *A61K 31/165* (2013.01); *A61K 31/167* (2013.01); *A61K 31/18* (2013.01); *A61K 31/19* (2013.01); *A61K 31/192* (2013.01); *A61K 31/4045* (2013.01); *A61K 31/4406* (2013.01); *A61K 31/4745* (2013.01); *A61K 31/506* (2013.01); *A61K 31/713* (2013.01); *A61K 35/766* (2013.01); *A61K 38/12* (2013.01); *A61K 38/15* (2013.01); *A61K 38/164* (2013.01); *A61K 39/0011* (2013.01); *A61K 39/02* (2013.01); *A61K 39/04* (2013.01); *A61K 39/12* (2013.01); *A61K 39/165* (2013.01); *A61K 39/17* (2013.01); *A61K 39/205* (2013.01); *A61K 39/285* (2013.01); *A61K 45/06* (2013.01); *A61K 2039/545* (2013.01); *C12N 2710/10343* (2013.01); *C12N 2760/20232* (2013.01); *C12N 2760/20243* (2013.01)

(58) Field of Classification Search
None
See application file for complete search history.

(56) References Cited

U.S. PATENT DOCUMENTS

| | | |
|---|---|---|
| 2007/0098743 A1 | 5/2007 | Bell et al. |
| 2009/0324587 A1 | 12/2009 | Goodwin et al. |
| 2010/0028380 A1 | 2/2010 | Kang et al. |
| 2010/0266636 A1 | 10/2010 | Richardson et al. |
| 2011/0044952 A1 | 2/2011 | Bell et al. |

FOREIGN PATENT DOCUMENTS

| | | |
|---|---|---|
| JP | 2007-215547 A | 8/2007 |
| JP | 2008-527051 A | 7/2008 |
| JP | 2009-519242 A | 5/2009 |
| JP | 2010-539192 A | 12/2010 |

(Continued)

OTHER PUBLICATIONS

Bridle et al. Vesicular stomatitis virus as a novel cancer vaccine vector to prime antitumor immunity amenable to rapid boosting with adenovirus. Mol Ther. Oct. 2009;17(10):1814-21. Epub Jul. 14, 2009.*

(Continued)

*Primary Examiner* — Nianxiang (Nick) Zou

(74) *Attorney, Agent, or Firm* — Gowling WLG (Canada) LLP

(57) ABSTRACT

A vaccination method is provided. The method comprises administering to a mammal a histone deacytelase inhibitor in conjunction with a vaccine that expresses an antigen to which the mammal has a pre-existing immunity.

17 Claims, 14 Drawing Sheets

(56) References Cited

FOREIGN PATENT DOCUMENTS

| WO | 03/088994 | 3/2003 |
| WO | 03/075952 | 4/2003 |
| WO | WO2010/105347 A1 | 9/2010 |

OTHER PUBLICATIONS

Nguyen et al. Chemical targeting of the innate antiviral response by histone deacetylase inhibitors renders refractory cancers sensitive to viral oncolysis. PNAS, Sep. 30, 2008, vol. 105, No. 39, p. 14981-14986.*

Karan et al. Paradoxical enhancement of CD8 T cell-dependent anti-tumor protection despite reduced CD8 T cell responses with addition of a TLR9 agonist to a tumor vaccine. Int. J. Cancer: 121, 1520-1528 (2007).*

Bridle et al. HDAC Inhibition Suppresses Primary Immune Responses, Enhances Secondary Immune Responses, and Abrogates Autoimmunity During Tumor Immunotherapy. Molecular Therapy vol. 21 No. 4, 887-894. 2013.*

Ta-Chiang Liu et al.: "Trichostatin A and Oncolytic HSV Combination Therapy Shows Enhanced Antitumoral and Antiangiogenic Effects", Molecular Therapy, vol. 16, No. 6, Apr. 1, 2008 (Apr. 1, 2008), pp. 1041-1047, XP055145940.

Bryam W Bridle et al.: "HDAC Inhibition Suppresses Primary Immune Responses, Enhances Secondary Immune Responses, and Abrogates Autoimmunity During Tumor Immunotherapy", Molecular Therapy, vol. 21, No. 4, Apr. 1, 2013 (Apr. 1, 2013), pp. 887-894, XP055145893.

Vanniasinkam, T. et al. "Trichostatin-A enhances adaptive immune responses to DNA vaccination" J. Clin, Virol, Aug. 2006. vol. 36, No. 4, pp. 292-297.

Lai, M-D et al. "An HDAC inhibitor enhances the antitumor activity of a CMV promoter-driven DNA vaccine." Cancer Gene Ther. Mar. 2010. vol. 17, No. 3, pp. 203-211.

Vo, D et al. "Enhanced anti-tumor activity induced by adoptive T cell transfer and the adjunctive use of the HDAC inhibitor LAQ824." Cancer Res. Nov. 15, 2009. vol. 69, No. 22, pp. 8693-8699.

Christiansen, A. et al. "Eradication of solid tumors using histone deacetylase inhibitors combined with immune-stimulating antibodies" PNAS. Mar. 8, 2011. vol. 108, No. 10, pp. 4141-4146.

Shen, L. et al. "Class I histone deacetylase inhibitor entinostat suppresses regulatory T cells and enhances immunotherapies in renal and prostate cancer models." Plos one. Jan. 27, 2012. vol. 7, Issue 1, e30815, pp. 1-14.

Mora-Garcia, M. et al. "Up-regulation of HLA class-I antigen expression and antigen-specific CTL response in cervical cancer cells by the demethylating agent hydralazine and the histone deacetylase inhibitor valproic acid." J. Translational Med. Dec. 27, 2006, vol. 4, No. 55.

Jaboin, J. et al., "MS-27-275, an inhibitor of histone deacetylase, has marked in vitro and in vivo antitumor activity against pediatric solid tumors" Cancer Res. Nov. 1, 2002. vol. 62, pp. 6108-6115.

Tao, R. et al. "Deacetylase inhibition promotes the generation and function of regulatory T cells." Nat. Med. Nov. 2007. vol. 13, No. 11, pp. 1299-1307.

Wang, L. et al. "Immunomodulatory effects of deacetylase inhibitors: therapeutic targeting of FOXP3+ regulatory T cells." Nat. Rev. Drug. Discov. Dec. 2009. vol. 8, No. 12, pp. 969-981.

Akimova, T. et al. "Histone/protein deacetylase inhibitors increase suppressive functions of human FOXP3+ Tregs." Clin. Immunol. Sep. 2010. vol. 136, No. 3, pp. 348-363.

* cited by examiner

Stats Summary
(general linear model)
Ad vs. Ad+VSV: p<0.0001
Ad vs. Ad+VSV+MS275: p<0.0002
Ad+VSV vs. Ad+VSV+MS275: not sig.

US 9,821,054 B2

METHOD OF VACCINATION COMPRISING A HISTONE DEACETYLASE INHIBITOR

FIELD OF THE INVENTION

The present invention relates generally to a method of vaccination, and in particular, relates to a vaccination method in which a viral vaccine is co-administered with a histone deacetylase inhibitor.

BACKGROUND OF THE INVENTION

Histone deacetylase inhibitors (HDACi) are epigenetic modifier drugs having broad effects on gene expression by virtue of impairing histone modifications required for controlling gene transcription. HDACi can modify interferon signalling in tumor cells and thus can be utilized as viral sensitizers to enhance oncolysis. By accentuating the inherent defects in interferon responsiveness of cancer cells, these drugs are able to increase the effectiveness of tumor-tropic viruses without rendering normal cells susceptible. Thus HDACI can alter innate immunity to facilitate viral oncolysis but their impact on acquired immune responses has not been investigated in this therapeutic setting.

Viral oncolysis and cancer immunotherapy exhibit clinical efficacy as stand-alone treatments. There is an ever-growing body of literature suggesting successful oncolytic virotherapy depends on its inherent ability to induce anti-tumor immunity, leading some to go so far as to define it as a form of immunotherapy. Several promising clinical candidates are viruses that have been engineered to express immunostimulatory transgenes. However, debate continues as to whether stimulating the immune system is of net benefit to oncolytic virotherapy. Indeed, if immune responses against the oncolytic vector were inadvertently promoted, this could compromise viral replication and harm the induction of tumor-specific responses, especially when self-antigens are targeted, via mechanisms such as antigen competition, where foreign viral antigens would have a marked advantage, and reduced antigen release due to less oncolysis. Therefore, optimal strategies to combine direct oncolysis with immunotherapy should aim to promote both anti-tumor immunity and oncolytic virus replication.

Oncolytic viruses have recently been shown to be particularly potent boosters of anti-tumor immune responses. This therapeutic approach combines conventional and oncolytic viral vaccines, both expressing the same tumor antigen. Boosting with an oncolytic vaccine can lead to both tumor debulking by the virus and a large increase in the number of tumor-specific CTL (cytotoxic T-lymphocytes) in primed animals. Paradoxically, this methodology actually generates larger anti-tumor immune responses in tumor-bearing, as compared to tumor-free, animals since the replicating oncolytic vector is amplified in the tumor leading to a very large increase in the number of antigen-specific TILs and eradication of established intracranial melanomas in some cases.

Several HDACi, including valproic acid (VPA), suberoylanilide hydroxamic acid (SAHA) and MS-275, are currently undergoing clinical investigations as anti-cancer drugs for various solid and hematological malignancies. Initial promising results have been obtained in acute myelogenous leukemia, T cell lymphomas and renal cell carcinoma. Interestingly, in addition to their direct anti-tumor activity, these HDACi have immunomodulatory properties. For instance, it has been shown that VPA, SAHA and MS-275 all can promote immunogenicity and immune recognition of cancer cells.

SUMMARY OF THE INVENTION

It has now been found that co-administration of HDACi with a boosting vaccine exhibits an enhanced effect.

Accordingly, in one aspect of the invention, a vaccination method is provided comprising the step of administering to a mammal a histone deacetylase inhibitor and a vaccine that delivers an antigen to which the mammal has a pre-existing immunity.

In another aspect of the invention, a composition is provided comprising a vaccine and a histone deacetylase inhibitor.

These and other aspects of the invention will become apparent in the detailed description that follows, by reference to the following figures.

DETAILED DESCRIPTION OF THE INVENTION

Figure 1:
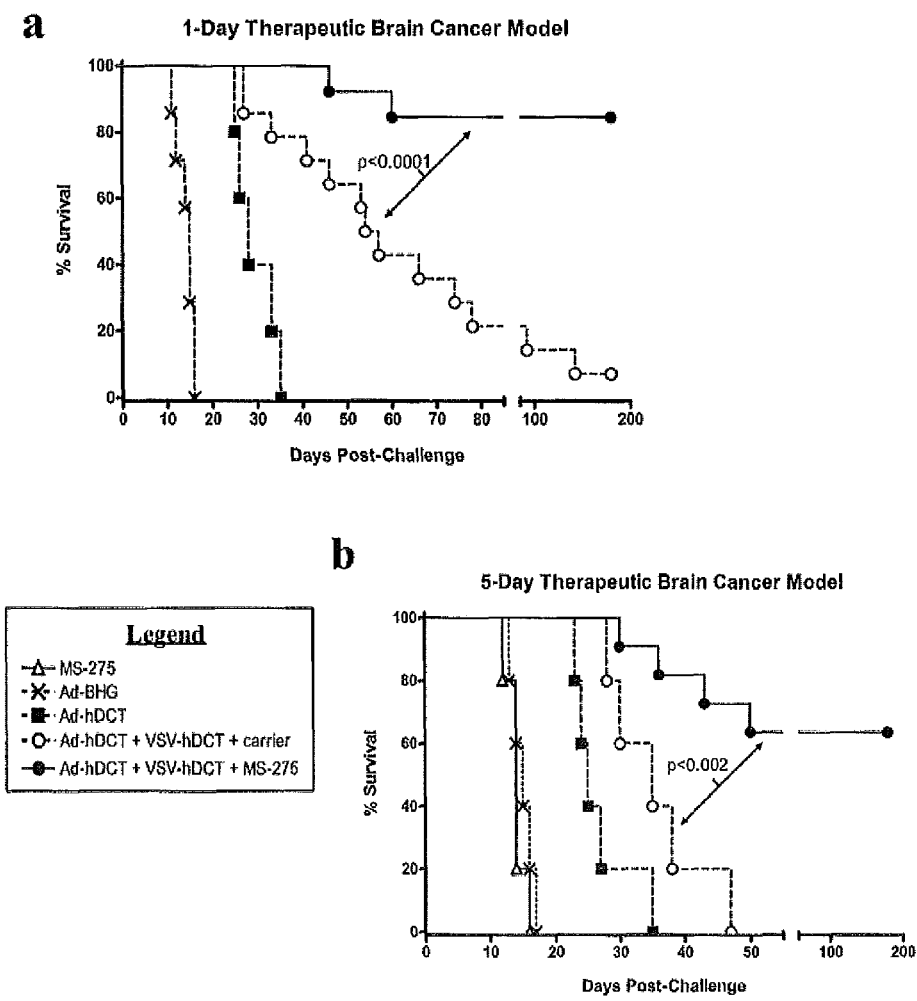
FIG. 1 illustrates the survival curves of a cancer model treated with PBS, Ad-BHG (negative control, $1\times10^8$ PFU IM), Ad-hDCT (TAA transgene, $1\times10^8$ PFU IM), Ad-hDCT+VSV-hDCT or Ad-hDCT+VSV-liDCT+MS-275 beginning at 1- or 5-days post-engraftment (A and B, respectively)

A vaccination method is provided comprising administering to a mammal a histone deacytelase inhibitor in combination with a vaccine adapted to express an antigen to which the mammal has a pre-existing immunity.

The term "vaccine" is used herein to refer to a biological preparation that induces an immunogenic response to a target antigen. Examples of vaccines include viral, bacterial, protein and nucleic acid vaccines. The term "viral vaccine" refers to a virus that induces an immunogenic response to a target antigen.

The term "mammal" refers to human as well as non-human mammals.

The present method includes administration to the mammal of a vaccine that delivers or expresses an antigen to which the mammal has a pre-existing immunity. As used herein, the term "pre-existing immunity" is meant to encompass an immunity induced by vaccination with an antigen, as well as a naturally existing immunity within the mammal resulting from a prior exposure to a given antigen.

To establish a pre-existing immunity, the present method may include a step of vaccinating a mammal with an antigen appropriate to induce an immune reaction against target cells, e.g. a priming step. Suitable antigens include tumour antigens, viral antigens, and in particular, antigens derived from viral pathogenic organisms such as HIV, HepC, FIV, LCMV, Ebola virus, as well as bacterial pathogens such as mycobacterium tuberculosis.

In one embodiment, the antigen is a tumour antigen, such as a tumor-associated antigen (TAA), e.g. a substance produced in a tumor cell which triggers an immune response in the mammal. Examples of such antigens include oncofetal antigens such as alphafetoprotein (AFP) and carcinoembryonic antigen (CEA), surface glycoproteins such as CA-125 and mesothelin, oncogenes such as Her2, melanoma-associated antigens such as dopachrome tautomerase (DCT), GP100 and MART1, cancer-testes antigens such as the MAGE proteins and NY-ESO1, viral oncogenes such as HPV E6 and E7, proteins ectopically expressed in tumours that are usually restricted to embryonic or extraembryonic tissues such as PLAC1. As one of skill in the art will appreciate, an antigen may be selected based on the type of cancer to be treated using the present method as one or more antigens may be particularly suited for use in the treatment of certain cancers. For example, for the treatment of melanoma, a melanoma-associated antigen such as DCT may be used. The term "cancer" is used herein to encompass any cancer, including but not limited to, melanoma, sarcoma, lymphoma, carcinoma such as brain, breast, liver, stomach and colon cancer, and leukaemia.

The antigen may be administered per se, or, preferably, administered via a vector, e.g. rhabdoviral, adenoviral (Ad), poxviral or retroviral vector, a plasmid or loaded antigen-presenting cells such as dendritic cells. Methods of introducing the antigen into the vector are known to those of skill in the art. Generally, the vector will be modified to express the antigen. In this regard, nucleic acid encoding the selected antigen is incorporated into the selected vector using well-established recombinant technology.

The antigen is administered to the mammal in any one of several ways including, but not limited to, intravenously, intramuscularly, or intranasally. As will be appreciated by one of skill in the art, the antigen, or vector incorporating the antigen, will be administered in a suitable carrier, such as saline or other suitable buffer. Following vaccination with a selected antigen, an immune response is generated by the mammal within an immune response interval, e.g. at least about 24 hours, preferably at least about 2-4 days or longer, e.g. at least about 1 week and possibly extending for months, years, or potentially life.

To establish an immune response to the antigen, vaccination using the antigen is conducted using well-established techniques. Accordingly, a selected antigen, or a vector expressing the antigen, may be administered to the mammal, in an amount sufficient to generate an immune response. As one of skill in the art will appreciate, the amount required to generate an immune response will vary with a number of factors, including, for example, the selected antigen, the vector used to deliver the antigen, and the mammal to be treated, e.g. species, age, size, etc. In this regard, for example, intramuscular administration of a minimum of at least about $10^7$ PFU of adenoviral vector to a mouse, or at least about $10^9$ PFU in a human, is sufficient to generate an immune response.

In another embodiment, the immune response to the antigen may be naturally-occurring within the mammal and a priming vaccination step is not necessary to induce the immune response. Naturally-occurring immune response to an antigen may result from any prior exposure to the antigen.

Once an immune response has been generated in the mammal to a given antigen, within a suitable immune response interval, a boosting vaccine adapted to deliver or express the antigen, such as a viral vaccine or an antigen-presenting cell, is then administered to the mammal in conjunction with an HDACi.

A viral vaccine expressing a selected antigen may be prepared by incorporating a transgene encoding the antigen into a suitable virus using standard recombinant technology. For example, the transgene may be incorporated into the genome of the virus, or alternatively, may be incorporated into the virus using a plasmid incorporating the transgene. Suitable viruses for use in this regard include oncolytic viruses, as well as both replicating (e.g. poxviral) and non-replicating (e.g. retroviral or adenoviral) vaccine vectors. The present method is not particularly restricted with respect to the oncolytic virus that may be utilized and may include any oncolytic virus capable of destroying tumour, while being appropriate for administration to a mammal. Examples of oncolytic viruses that may be utilized in the present method include rhabdoviruses such as vesiculoviruses, e.g. vesicular stomatitis virus (VSV) and Maraba viruses, Ephemerovirus, Cytorhabdovirus, Nucleorhabdovirus and Lyssavirus viruses, as well as measles, vaccinia, herpes, myxoma, parvoviral, Newcastle disease, adenoviral and semliki forest viruses.

The antigen-expressing virus is administered in an amount suitable to boost the immune response resulting from the pre-existing immunity in conjunction with an HDACi. In one embodiment, a tumour antigen-expressing oncolytic virus is administered in an amount suitable for oncolytic viral therapy in conjunction with an effective amount of an HDACi. The amount of each will vary with at least the selected virus, the selected HDACi and the mammal to be treated, as will be appreciated by one of skill in the art. For example, a minimum of $10^8$ PFU of oncolytic VSV administered IV to a mouse is sufficient for oncolytic therapy. A corresponding amount would be sufficient for use in a human.

The viral vaccine is administered in conjunction with an HDACi. Suitable histone deacetylase inhibitors (HDACi) in accordance with the invention include, but are not limited to, hydroxamic acids such as vorinostat (SAHA), belinostat (PXD101), LAQ824, trichostatin A and panobinostat (LBH589); benzamides such as entinostat (MS-275), C1994, and mocetinostat (MGCD0103), cyclic tetrapeptides (such as trapoxin B), and the depsipeptides, electrophilic ketones, and the aliphatic acid compounds such as phenylbutyrate and valproic acid. A therapeutic amount of HDACi is administered to a mammal in the present method, e.g. an amount sufficient to enhance the immunological response to the viral vaccine. The HDACi may be administered using any suitable administrable form, including for example, oral, subcutaneous, intravenous, intraperitoneal, intranasal, enteral, topical, sublingual, intramuscular, intra-arterial, intramedullary, intrathecal, inhalation, ocular, transdermal, vaginal or rectal means.

The viral vaccine and histone deacetylase inhibitor may be administered in accordance with methods of the invention alone or combined together in a composition, and may also be combined with one or more pharmaceutically acceptable adjuvants or carriers. The expression "pharmaceutically acceptable" means acceptable for use in the pharmaceutical arts, i.e. not being unacceptably toxic, or otherwise unsuitable for administration to a mammal. Examples of pharmaceutically acceptable adjuvants include, but are not limited to, diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule, lozenge, solution or suspension in an aqueous or non-aqueous liquid, an oil-in-water or water-in-oil liquid emulsion, an elixir or syrup are prepared using adjuvants including sugars, such as lactose, glucose and sucrose; starches such as corn starch and potato starch; cellulose and derivatives thereof; including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, disintegrating agents, anti-oxidants, preservatives, colouring agents and flavouring agents may also be present. In another embodiment, the composition may be formulated for application topically as a cream, lotion or ointment. For such topical application, the composition may include an appropriate base such as a triglyceride base. Such creams, lotions and ointments may also contain a surface-active agent and other cosmetic additives such as skin softeners and the like as well as fragrance. Aerosol formulations, for example, for nasal delivery, may also be prepared in which suitable propellant adjuvants are used. Compositions of the present invention may also be administered as a bolus, electuary, or paste. Compositions for mucosal administration are also encompassed, including oral, nasal, rectal or vaginal administration for the treatment of infections, which affect these areas. Such compositions generally include one or more suitable non-irritating excipients or carriers comprising, for example, cocoa butter, polyethylene glycol, a suppository wax, a salicylate or other suitable carriers. Other adjuvants may also be added to the composition regardless of how it is to be administered, which, for example, may aid to extend the shelf-life thereof.

The present method provides an effective synergistic vaccination in a mammal in which primary immune responses are impaired, while the secondary immune response to a given antigen is enhanced, e.g. enhanced by at least about 2-fold or greater, e.g. about 4-fold or greater, e.g. about 6 to 8-fold or greater, in comparison to the response induced by the viral vaccine alone. A contributing factor to this effect is the selective lymphopenia induced by the method whereby naïve lymphocytes are selectively depleted by the combination. The combination of histone deacetylase inhibitor with the vaccine booster also reduces the autoimmune sequelae resulting from vaccination against an autoantigen without reducing the effects, e.g. anti-tumor effects, of such vaccination.

In one embodiment, a method of boosting an immune response in a mammal having a pre-existing immunity to an antigen is provided in which the antigen is administered to the mammal, for example intravenously, via a vector that is capable of infecting B-cells, via antigen-presenting cells such as B cells, by a vector that induces expression of type I interferon or via a vector in combination with an agent that induces expression of type I interferon to achieve a vaccination in which the antigen immune response is enhanced and the primary immune response is impaired. The term "pre-existing immunity" is as defined above and may be achieved as described above. This method may be utilized to boost immunity with respect to any antigen, including for example, tumour antigens, viral antigens and particularly antigens derived from viral pathogenic organisms such as HIV, HepC, Hy, LCMV, Ebola virus, as well as bacterial pathogens such as mycobacterium tuberculosis.

As one of skill in the art will appreciate, the vector may be prepared to express a selected antigen using well-established recombinant technology. Appropriate vectors for use in delivering an antigen to the mammal preferably include vectors that induce expression of type I interferon, such as, for example, rhabdoviruses as set out above, including vesiculoviruses and Maraba-based viruses. Mutant viral vectors are also appropriate for use in the present method. Mutant attenuated virus, including replication incompetent forms, are particularly advantageous for use in the present method.

The antigen-expressing vector may be combined with an agent that induces expression of type I interferon. Examples of such agents include toll-like receptor (TLR) ligands or adjuvants including, but not limited to, imiquimod, polyinosine-polycytidylic acid (polyI:C), CpG ODN, imidazoquinoline, monophosphoryl lipid A, flagellin, FimH and N-glycolyted muramyldipeptide. To achieve a vaccination in which the antigen immune response is enhanced and the primary immune response is impaired, the vector is combined with an amount of type I interferon-inducing agent sufficient to induce interferon and cause the lympopenia.

Once the vector is prepared to express the selected antigen, it is administered, e.g. intravenously, to the mammal for optimal immunity boosting in conjunction with an HDACi as described above. The amount of vector administered will again vary with the selected vector, as well as the mammal. In relation to the pre-existing immunity, the antigen-expressing vector may be administered to the mammal prior to or coinciding with the peak immune response of the pre-existing immunity. The antigen-expressing vector is optimally administered to the mammal to boost the pre-existing immunity following the effector phase of the priming of the pre-existing immunity.

Embodiments of the invention are described by reference to the following specific examples which are not to be construed as limiting.

EXAMPLE

Methods

Mice

Female, age-matched (8-10 weeks old at initiation of experiments) C57BL/6 mice were purchased from Charles River Laboratories (Wilmington, Mass.) and housed in a controlled environment in the Central Animal Facility at McMaster University with food and water provided ad libitum. All animal experimentation was approved by McMaster University's Animal Research Ethics Board and complied with the Canadian Council on Animal Care guidelines.

Viral Vectors

The replication-deficient rHuAd5-hDCT vector had E1/E3 deleted, expressed the full-length hDCT gene and was propagated in 293 cells and purified on a CsCl gradient. Replication-competent rVSV-hDCT and rVSV-GFP have been described (Stojdl et al. (2003). *Cancer Cell,* 4(4), 263-275). The rHuAd5-BHG and rVSV-MT were control vectors lacking a transgene.

Prime-Boost Protocol

Mice were primed by intramuscular injection of $1 \times 10^8$ pfu of rHuAd5. For boosting, $1 \times 10^9$ pfu of rVSV was injected i.v. at a 14-day interval. For the HDACi treatment, MS-275 (dissolved in DMSO and diluted in saline) was co-administered with VSV administration and for the following 4 days, 0.1 mg given IP.

Cancer Model

To establish brain tumors, mice received intracranial injections of $1 \times 10^3$ B16-F10 cells in 1 µl of PBS. Mice were placed in a stereotaxis (Xymotech Biosystems Inc, Quebec, Canada) and an incision made in the scalp with a scalpel blade to expose the skull under anaesthesia. A small burr hole was drilled through the skull at the injection site. Cells were injected with a 26-gauge needle mounted on a 10 µl Hamilton syringe (Hamilton Company, Reno, Nev.) at the following site in the right hemisphere of the brain (relative to bregma): 0.62 mm anterior, 2.25 mm lateral and 4.0 mm deep. Cells were injected over a period of 1 minute and the needle was left in place for 2 minutes prior to withdrawal to minimize reflux along the injection tract. The scalp incision was closed with stainless steel clips that were removed 7-10 days later.

Peptides

The immunodominant peptide from DCT that binds to $H-2K^b$ ($DCT_{180-188}$, SVYDFFVWL) was synthesized by PepScan Systems (Lelystad, The Netherlands). The $H-2K^b$-restricted epitope from the N protein of VSV (RGYVYQGL) was purchased from Biomer Technologies (Hayward, Calif.).

Antibodies/Tetramers

Monoclonal antibodies recognizing the following targets were used for flow cytometry assays: CD16/CD32 (Fe Block), CD3 (145-2C11), CD4 (RM4-5), CD8 (53-6.7), IFN-γ (XMG1.2), TNF-α (MP6-XT22), CD19 (1D3), B220 (RA3-6B2), NK1.1 (PK136), KLRG-1, CD44 (1M7), CD62L (MEL-14), CD107a (1D4B), $H-2K^b$ (AF688.5) and $1-A^b$ (25-9-17) (from BD Biosciences, Mississauga, ON, Canada) and Foxp3 (FJK-16s) (eBioscience, San Diego, Calif., USA).

Detection of Antigen-Specific T Cell Responses

Single cell suspensions prepared from different tissues were re-stimulated with peptides (1 µg/ml) at 37° C. for 5 hrs and brefeldin A (Golgi Plug, 1 µg/ml; BD Biosciences) was added during the last 4-hrs of incubation. Cells were treated with Fe block and stained for surface expression of CD3 and CD8. Cells were subsequently fixed, permeabilized (Cytofix/Cytoperm, BD Biosciences) and stained for intracellular IFN-γ and TNF-α. Data were acquired using a FACSCanto with FACSDiva software (BD Biosciences) and analyzed with FlowJo software (Tree Star, Ashland, Oreg.).

T Cell Functional Avidity Assay

Splenocytes were exposed to a dilution series of the SVY peptide such that lower and lower concentrations were provided. The cells were treated with Golgi plug during this stimulation and assessed by flow cytometry to measure IFNγ by intracellular staining as above.

Quantification of DCT-Specific Antibodies

U2OS cells engineered to express DCT were plated into multiwell plates and grown to confluence. The cells were then fixed and permeabilized. Sera from treated mice were serially diluted and used to probe these fixed monolayers. Following incubation the unbound antibody was washed away and the bound DCT-specific antibodies were detected with an anti-mouse secondary bearing a fluorescent tag. The fluorescent signal was detected to measure the titre of anti-DCT antibody present in the sera.

Statistical Analyses

GraphPad Prism for Windows (GraphPad Software, San Diego, Calif., USA) was used for graphing. For statistical analyses, GraphPad Prism and Minitab Statistical Software (Minitab Inc., State College, Pa., USA) were used. If required, data were normalized by log transformation. Student's two-tailed t-test, one- or two-way ANOVA or general linear modeling was used to query immune response data. Differences between means were considered significant at $p \leq 0.05$. Means plus standard error bars are shown. Survival data were analyzed using the Kaplan-Meier method and the logrank test.

Results

MS-275 Dramatically Improves the Therapeutic Outcome in Combination with an Oncolytic Booster Vaccine To determine the potential synergistic effect of MS-275 with a prime-boost regimen as described in WO2010/105347 A1, an aggressive brain melanoma model was used with a defined melanoma-associated antigen, dopachrome tautomerase (DCT), which is expressed by the melanoma cell line B16-F10 as well as normal melanocytes (Bridle JI/MT). One- or 5-days after intracranial inoculation of B16-F10 cells, mice were treated sequentially with a recombinant human type 5 adenoviral vector expressing human DCT (rHuAd5-hDCT) and an oncolytic recombinant VSV expressing the same antigen (rVSV-hDCT) at a 14-day interval. With the goal of enhancing oncolysis, MS-275 was administered in the context of boosting with rVSV. This also coincided with the persistence of rVSV and the peak of the boosted CTL response. The data in FIGS. 1*a* and *b* show that the average survival in untreated animals was 15 days confirming the aggressiveness of this model with a small treatment window. Vaccination with rHuAd5-hDCT alone prolonged animal survival to a median of 28 and 25 days in the 1- and 5-day therapeutic models, respectively. Subsequent delivery of the oncolytic vaccine, rVSV-hDCT, significantly enhanced animal survival (FIG. 1a). Despite the improvement of the survival rate, however, most animals treated with the prime-boost regimen ultimately succumbed to tumor progression, especially in mice bearing 5-day-old tumours (FIG. 1b), consistent with previous observations. Concomitant treatment with MS-275 at the time of rVSV-hDCT delivery dramatically enhanced the efficacy of the combination treatment and cured 85% (n=13) and 64% (n=11) of mice bearing one- or 5-day-old tumors, respectively, at the initiation of treatment. MS-275 alone had no effect on efficacy in this cancer model despite in vitro inhibition of B16-F10 cell growth.

The Magnitude of NK Cell and Secondary Tumor-Specific CTL and Antibody Responses is Preserved in the Presence of MS-275

Figure 2:
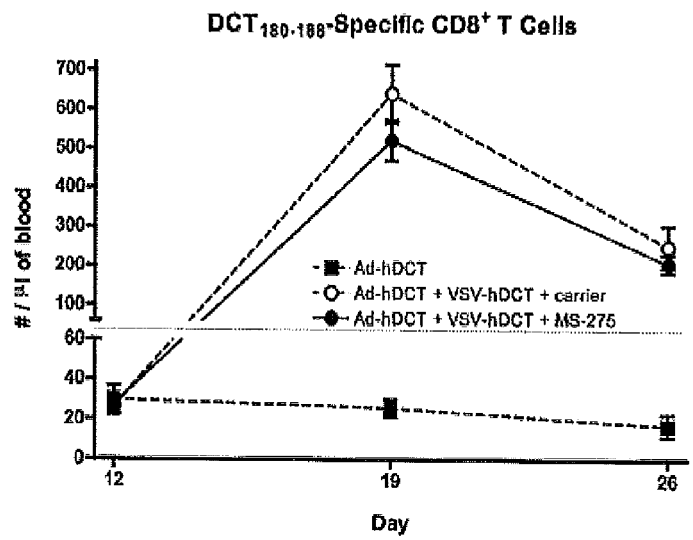
FIG. 2 graphically illustrates that co-administration of an oncolytic vaccine booster with an HDACi maintains tumour-antigen specific responses (A), tumour antigen-specific antibody responses (B), number of activated NK cells (C), enhances the co-expression of IFNγ and TNFα (D), enhances the amount of IFNγ (E) and TNFα (F) expressed by tumour antigen-specific T cells following oncolytic vaccine boosting, and enhances the T cell avidity (G)
Figure 2:
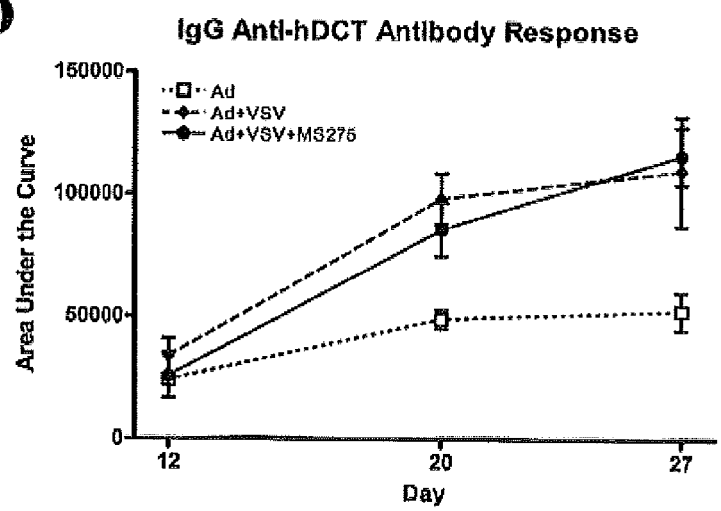
Figure 2:
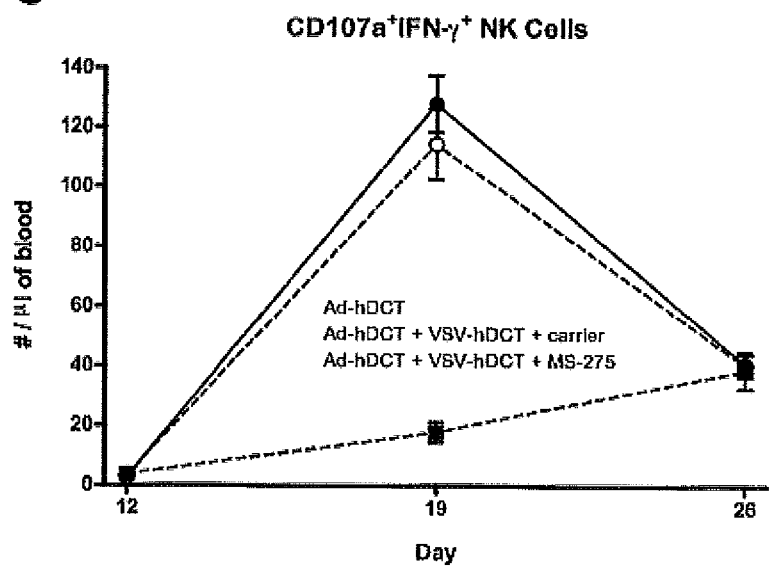
Figure 2:
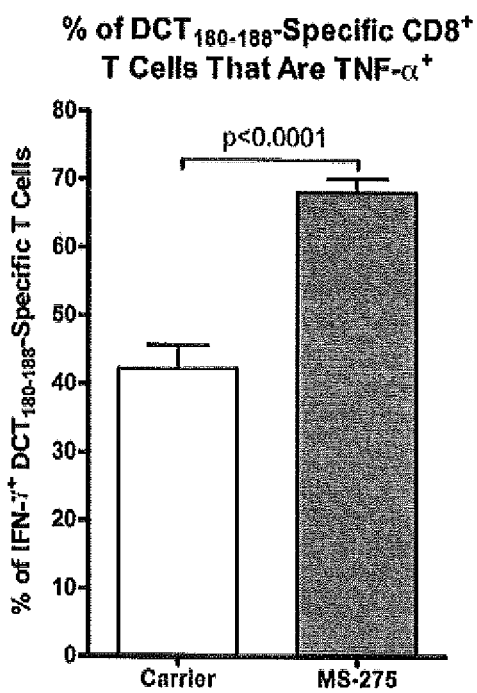
Figure 2:
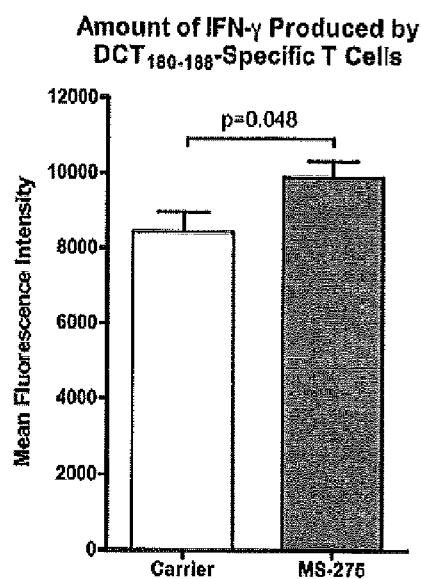
Figure 2:
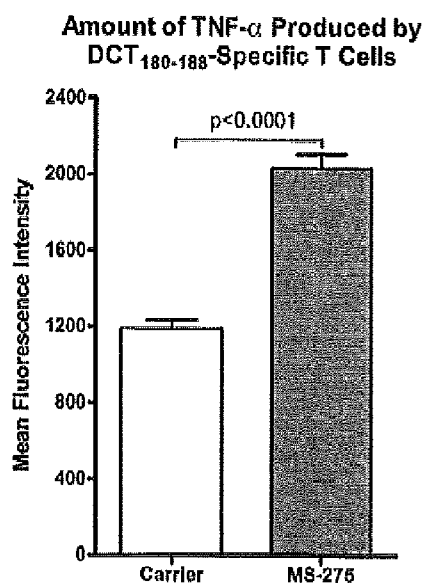
Figure 2:
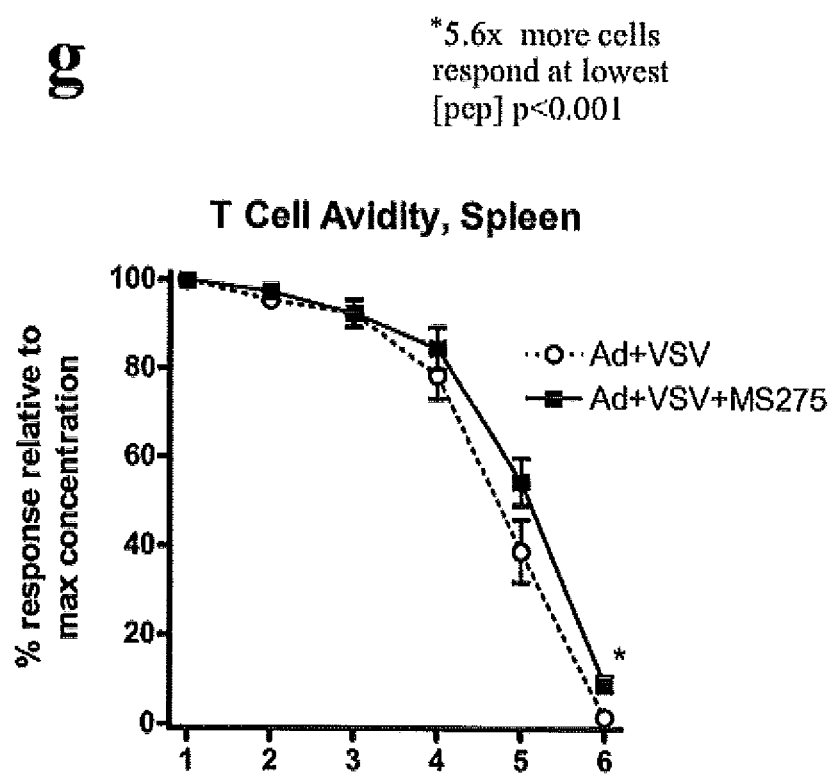

The efficacy of prime-boost vaccination in this model directly correlated with the magnitude of tumor-specific $CD8^+$ T cell responses. Given that the impact of HDAC inhibition on immune responses during oncolytic viral therapy has not been investigated it was determined whether or not this crucial component of the therapy was enhanced, leading to the dramatic improvement in efficacy. DCT-specific, IFN-γ-producing $CD8^+$ T cells were quantified in the circulation at days 5 and 12 post-rVSV booster vaccination, based on the previous observation where the secondary T cell response induced by rVSV reached its peak at day 5 and declined after 12 days. The magnitude of the DCT-specific $CD8^+$ T cell response was unaffected by MS-275 (FIG. 2a). In parallel, DCT-specific IgG antibodies in plasma were measured using an in-cell Western blotting assay (FIG. 2b). These results revealed a previously unappreciated aspect of the therapy; namely, that tumor-specific antibodies, like the T cells, were significantly boosted. Similar to the T cells, the secondary antibody response was not affected by MS-275. It was also found that booster vaccination with rVSV increased the number of circulating NK cells that were capable of producing IFN-γ and undergoing degranulation (based on CD107a expression) but MS-275 did not affect this (FIG. 2c). Overall, these findings suggest that the improved therapeutic effect of MS-275 was not due to induction of higher-magnitude effector responses.

Enhanced Efficacy with MS-275 Correlates with Improved CTL Quality

Compared to rHuAd5/rVSV alone, the addition of MS-275 increased the frequency of $CD8^+$ T cells that co-expressed TNF-α (FIG. 2d) and the intensity of their TNF-α (FIG. 2e) and IFN-γ production (FIG. 20). This suggests that MS-275 may improve the quality of activated $CD8^+$ T cells. Better quality T cells are often associated with higher avidity cognate interactions with MHC-peptide complexes (ref). Therefore, the functional avidity of T cells from mice treated with or without MS-275 was determined. To acquire enough cells for this assay, splenocytes were used. These cells were exposed to serial dilutions of the immunodominant peptide from DCT ($DCT_{180-188}$; concentration range: 1 ug/ml to 10 pg/ml). Interestingly, 5.6× more $CD8^+$ T cells could respond to the lowest concentration of peptide when mice received HDACi treatment (FIG. 2g).

MS-275 causes Lymphopenia During VSV Booster Vaccination

Figure 3:
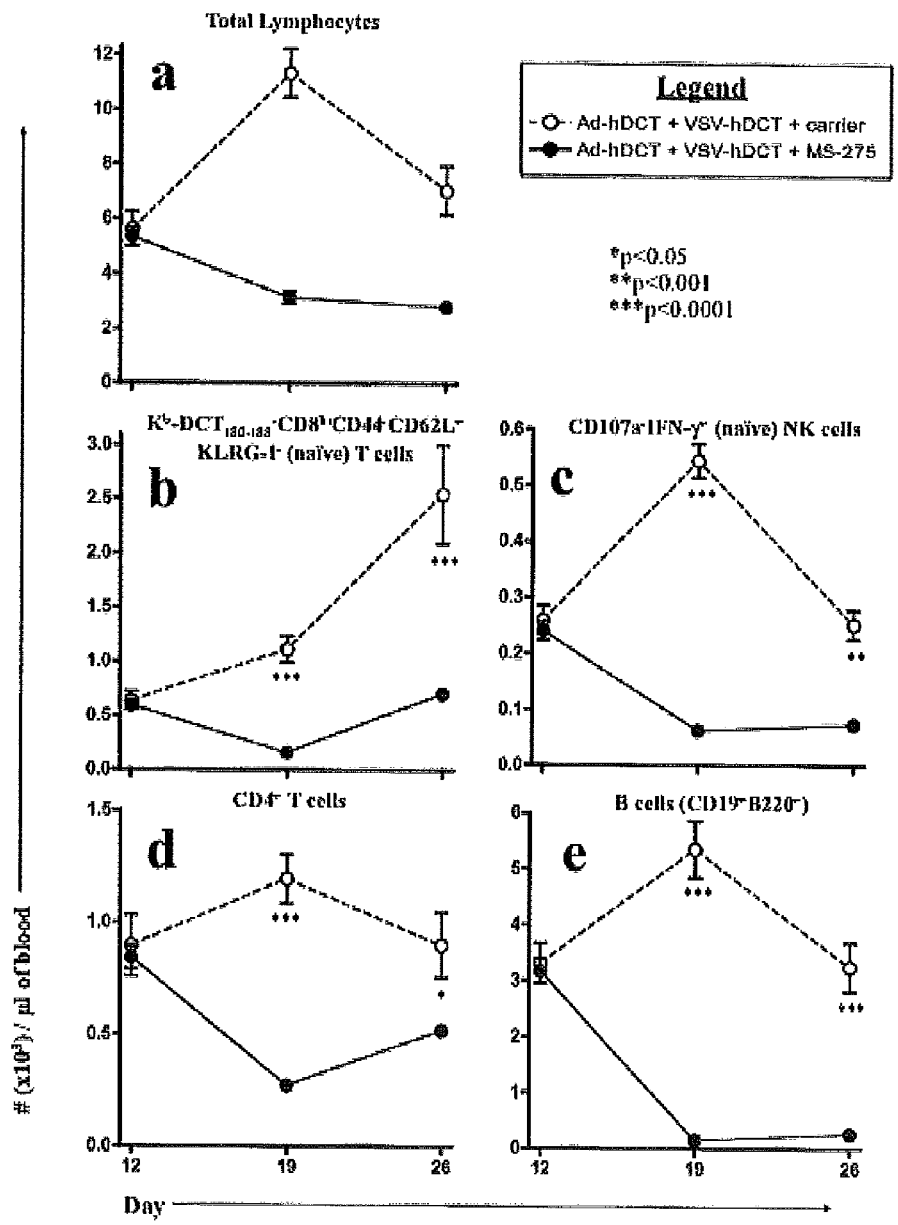
FIG. 3 graphically illustrates that co-administration of an oncolytic vaccine booster with an HDACi produces a profound lymphopenia as evidenced by a reduction of total lymphocyte counts in the peripheral blood attributed to a reduction in naïve CD8+ cells (B), naïve NK cells (C), CD4+ T cells (D) and B cells (E)

Surprisingly, although the number of tumor-specific CTL and activated NK cells were not influenced by MS-275 treatment, a transient but severe lymphopenia in the treated mice was observed (FIG. 3a). Indeed, a closer examination indicated that MS-275 provoked a profound loss of circulating naïve $CD8^+$ T cells ($CD8^{high}CD44^-CD62L^+KLRG$-$1^-$) (FIG. 3b) and resting NK cells ($CD107a^-IFN$-$γ^-$) (FIG. 3c) were substantially reduced during treatment with MS-275. Furthermore, a 77% reduction of total $CD4^+$ T cells was seen at the same timepoint (FIG. 3d). These affected cell populations started to recover one week after the peak of the boosted CTL response likely due to cessation of MS-275 treatment and VSV clearance. Most strikingly, 97% of B cells were eliminated and their recovery was much slower than other cell populations (FIG. 3e). This lytnphopenic effect was not dependent on the presence of a tumor (data not shown) nor was it strain-specific (FIG. 6), suggesting that it is a general phenomenon. These results reveal a novel property of MS-275 that allows secondary expansion of $CD8^+$ T cells and antibodies while simultaneously eliminating other lymphocyte populations including naïve T, B and NK cells. This lymphopenic environment may not only provide more physical space and growth factors to promote expansion and function of effector cells but may also modulate the outcome of immune responses against VSV and its oncolytic effect.

Similar results were achieved using the HDACi, CI-994.

Figure 7:
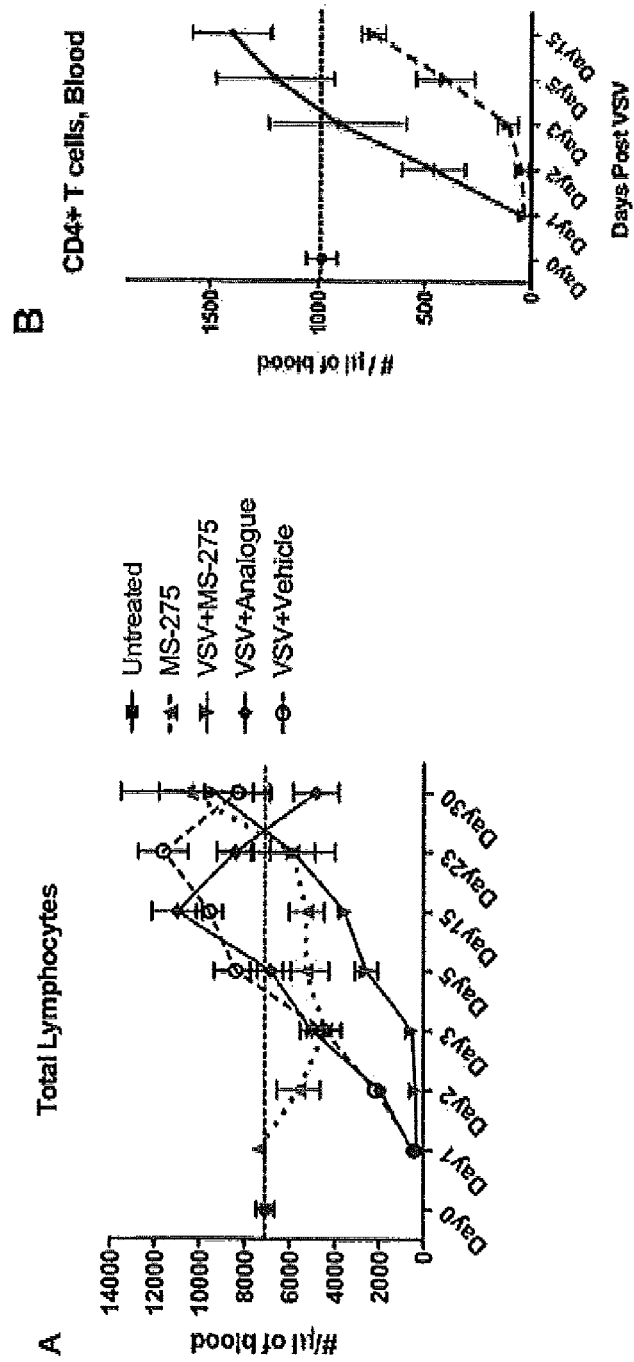
FIG. 7 graphically illustrates that VSV induces a transient lymphopenia that is significantly extended by MS-275 co-administration as evidenced by total lymphocyte counts (A), naïve CD4+ cells (B), CD8+ T cells (C) and B cells (D). Horizontal dotted line represents average count for untreated mice.
Figure 7:
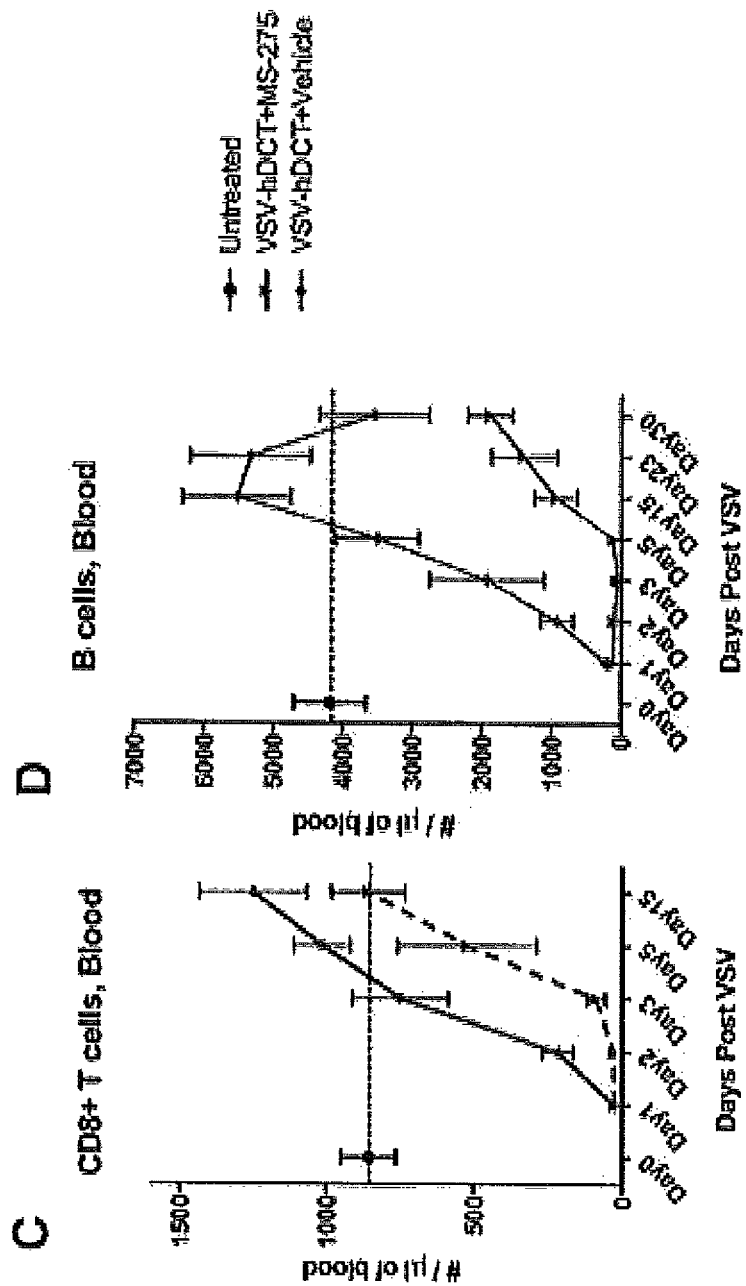

FIG. 7 illustrates total lymphocyte conts measured in the peripheral blood of mice over a 30-day period. Number of cells per µl of blood were determined over a 30 day period post-treatment. The virus alone induces a very transient lymphopenia that is significantly extended by co-admnistration of an HDACi drug (MS-275), while the drug alone has a modest effect. Importantly a drug analogue that lacks HDAC inhibitory properties has no effect here indicating the requirement for HDAC inhibition. These effects extend to CD4+ and CD8+ T cells as well as B cells.

Figure 4:
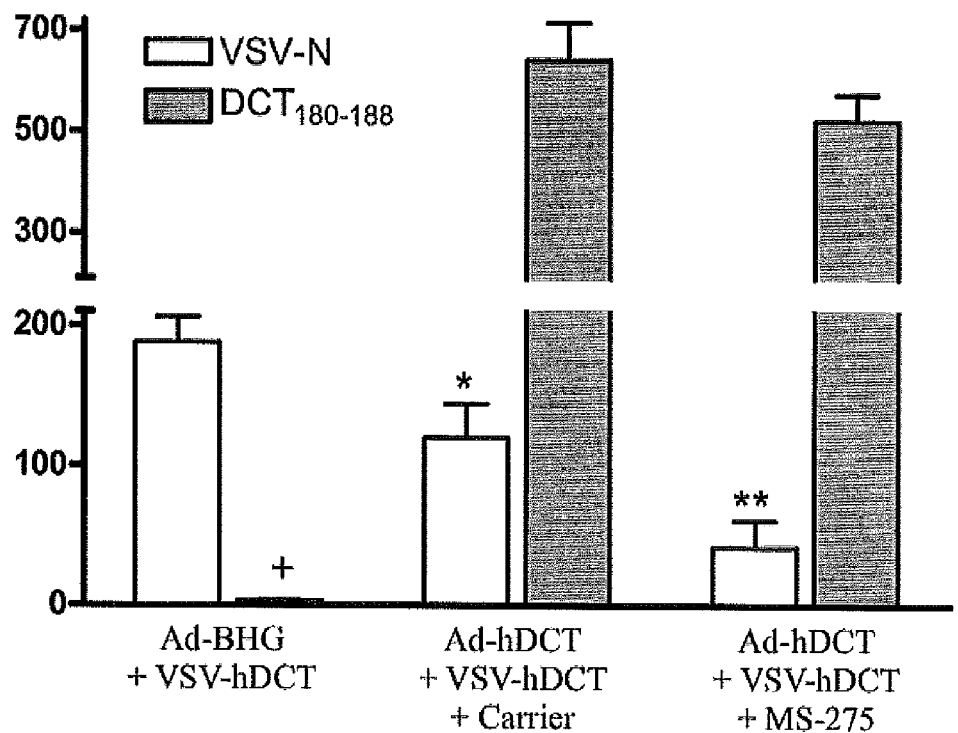
FIG. 4 graphically illustrates that co-administration of all oncolytic vaccine booster with an HDACi reduces anti-viral responses while maintaining anti-tumour responses.

The ability of MS-275 to impair primary immune responses prompted a determination of whether or not it could attenuate the immune response against the rVSV boosting vector. To evaluate this, $CD8^+$ T cell responses against a $K^b$-restricted immunodominant epitope from the N-protein of rVSV were measured at day 7 post-rVSV inoculations. As shown in FIG. 4a, while the number of DCT-specific CTL was not affected by MS-275 treatment, rVSV-reactive CTLs were significantly reduced suggesting that MS-275 differentially influences expansion of memory and naïve $CD8^+$ T cells.

Altogether, these results point to a great benefit of combining MS-275 with an oncolytic virus-based booster vaccine that leads to a focused immune response against the tumor while delaying the response against the oncolytic virus, allowing for extended viral oncolysis.

Agents that Induce Interferon Type I Expression Induce a Lymphopenia that is Extended by MS-275 Co-Administration.

Figure 8:
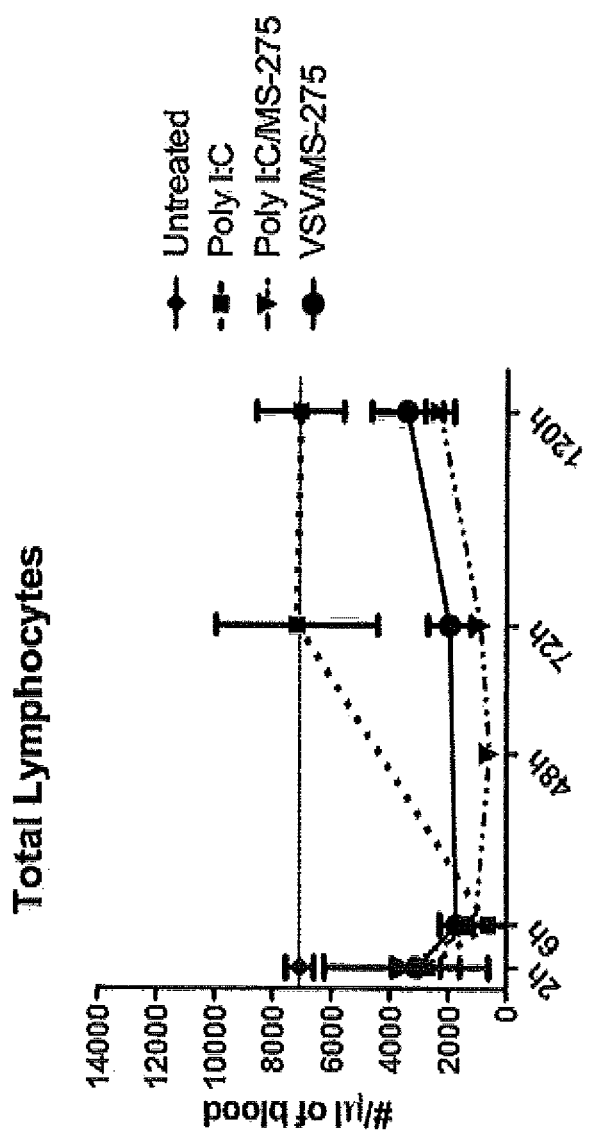
FIG. 8 graphically illustrates lymphopenia induced by co-administration of Poly I:C with MS-275 as compared with administration of Poly I:C alone and VSV/MS-275 as evidenced by total lymphocyte counts.

Female mice (8-10 weeks old C57BL/6) were treated with a single dose of PolyI:C (200 µg in 100 µl of phosphate-buffered saline, Sigma) and were treated with 0.1 mg of MS-275 once a day for 5 days via intraperitoneal injection as the PolyI:C combination MS-275 treatment group. PolyI:C is a classic inducer of type I interferon expression. Mice treated with a single dose of PolyI:C only were regarded as PolyI:C treatment group, whereas mice treated with five doses of MS-275 for 5 days represent the drug only treatment group. Blood was taken from the periorbital sinus and red blood cells were lysed with ACK lysis buffer. Peripheral blood lymphocyte counts were assessed at 2 h, 6 h, 24 h, 48 h, 72 h and 120 h after PolyI:C injection (N=3) as shown in FIG. 8. Data were collected by a FACSCanto flow cytometer with FACSDiva 5.0.2 software (BD Pharmingen) and analyzed with FlowJo Mac (Treestar, Ashland, Oreg.). In the absence of virus, PolyI:C generates an identical lymphopenia that is extended by the drug. Thus, the drug induces these effects in the presence of inducers of interferon.

Figure 5:
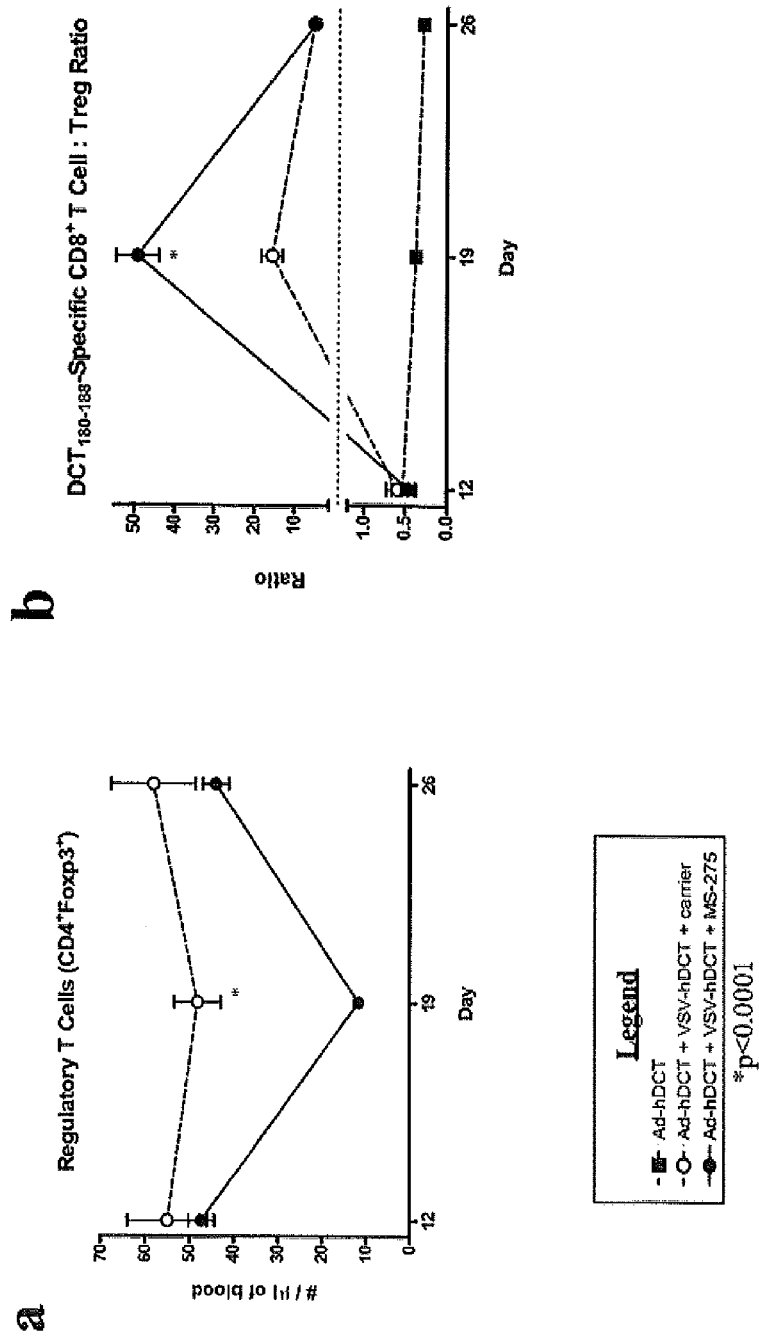
FIG. 5 graphically illustrates that co-administration of an oncolytic vaccine booster with an HDACi reduces Treg frequencies (A), increases tumour antigen-specific T cell:Treg ratio (B) and reduces Foxp3 expression levels (C)
Figure 5:
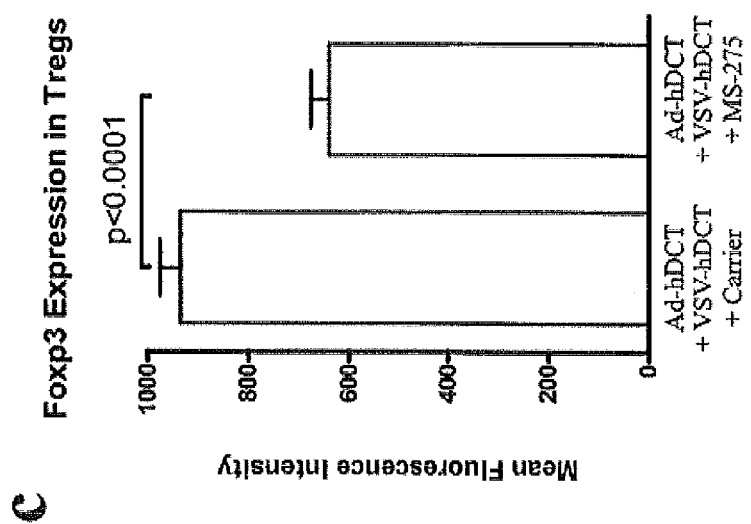

MS-275 Reduces Tregs, Especially those that Express a High Level of Foxp3 and Up-Regulates MHC Expression on Tumor Cells The lymphopenia, especially the reduction of total $CD4^+$ T cells, induced by MS-275 in the model led to the assessment of its direct impact on $CD4^+Foxp3^+$ Tregs. Data in FIG. 5a show that the number of Tregs was significantly decreased (75% reduction) during booster immunization, though it appeared to bounce back faster than other cell populations (FIG. 3a-e). This led to more than a 3-fold increase in the DCT-specific $CD8^+$ to Treg cell ratio (FIG. 5b). Notably, the intensity of Foxp3 expression by Tregs was significantly lower in mice upon MS-275 treatment (FIG. 5c) suggesting the drug may selectively remove Foxp3 high Tregs that have stronger suppressive function. Together, these data demonstrate that MS-275 can directly downregulate Treg activities, at least in the context of an oncolytic booster vaccine, allowing the massive secondary $CD8^+$ T cell responses to function in a less stringently regulated environment.

MS-275 Prevents Vaccine-Induced Autoimmune Vitiligo

Figure 6:
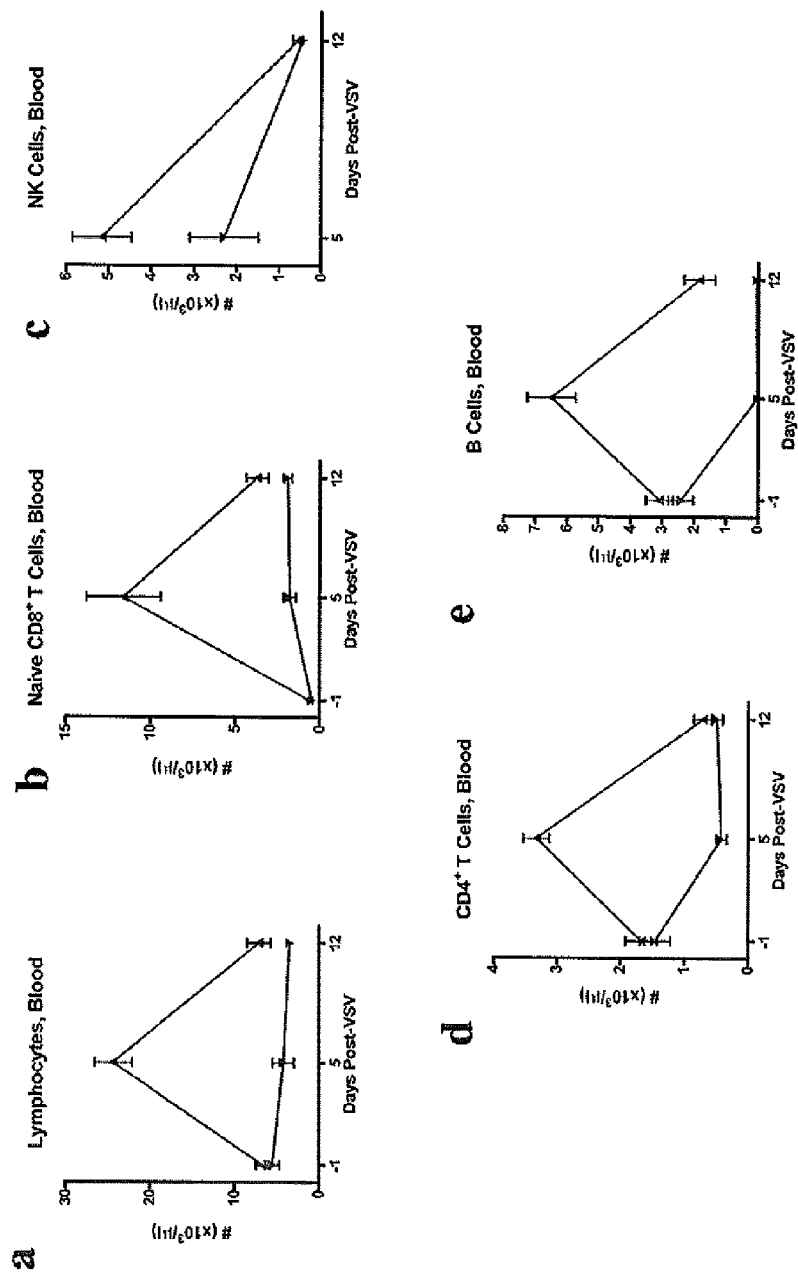
FIG. 6 graphically illustrates the lymphopenia induced by co-administration of an oncolytic vaccine booster with an HDACi is not strain-specific as similar reductions in total lymphocytes (A), naïve CD8+ T cells (B), total NK cells (C), CD4+ T cells (D) and B cells (E) occurred in Balb/c mice as in C57/B6 mice.

The oncolytic vaccine vector utilized here leads to a very potent immune response against an auto-antigen expressed in normal melanocytes, leading to severe autoimmune vitiligo in those mice treated with both rHuAd5-hDCT and rVSV-hDCT (FIG. 6, representative of multiple mice in each group from 4 experiments). Given that MS-275 co-administration significantly reduces Treg frequencies in these mice one might predict that the drug would exacerbate this autoimmune pathology. Remarkably, the induction of systemic vitiligo by prime-boost vaccination was almost completely abolished by concomitant treatment with MS-275, in stark contrast to its enhancement of anti-tumor efficacy. This suggests that a pharmacological drug may achieve separation of unwanted autoimmune sequelae from anti-tumor immunity during vaccination therapy against self-tumor antigens.

Co-Administration of VSV and MS-275 Depleted Immature Lymphocyte Precursors in Bone Marrow and Thymus.

Figure 9:
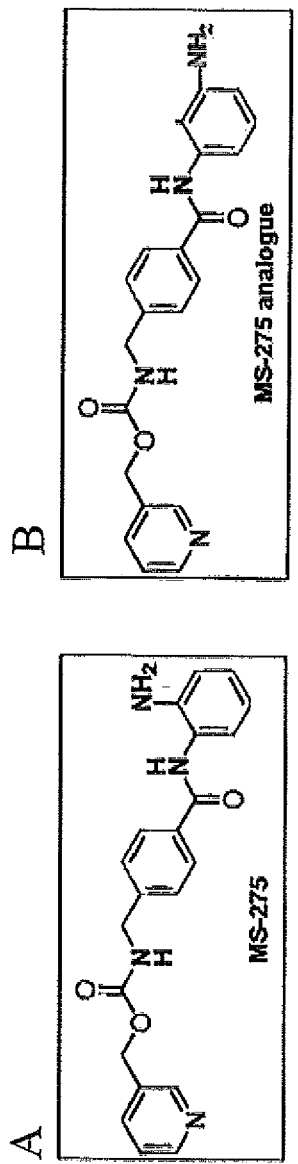
FIG. 9 illustrates the structure of MS-275 (A) and an inactive MS-275 analogue (B).

Mice were infected with a single tail-vein injection (i.v.) dose of VSV ($2\times10^9$ PFU VSV in 200 µl of phosphate-buffered saline) and were treated with 0.1 mg of MS-275 via intraperitoneal injection once a day for 3 days as VSV combination MS-275 treatment group. Mice infected with a single dose of VSV only were regarded as VSV treatment group, whereas mice treated with three doses MS-275 or MS-275 analogue (as shown in FIG. 9) for 3 days were drug only or analogue only treatment groups respectively, naïve mice were not treated with virus or drug. (N=3) Lymphocytes from thymus or bone marrow (femur and tibia) were harvested 3 days after VSV injection. Cells were then treated with anti-CD16/32 and surface markers fluorescently labelled by antibodies for CD4/CD8 or B220/IgM (BD Pharmingen). Lymphocyte progenitors were depleted by the combination therapy in both thymus (immature T cells) and bone marrow (immature B cells). Thus, the extended lymphopenia is due in part to reduction in progenitors that can replace depleted lymphocytes in periphery.

Discussion

When used in conjunction with an oncolytic vaccine therapy, MS-275, a benzamide class inhibitor of type 1 HDACs, not only enhances viral replication and MHC expression within the tumor but also has profound effects on the acquired arm of the immune system. This combination therapy leads to a selective lymphopenia that impairs both cellular and humoral immune responses against the oncolytic virus while significantly reducing Tregs thus generating a focused and derepressed immune response versus the tumour. By deleting the undesirable immune cells and maintaining those that are beneficial, this combination provides the best of both worlds, where the immune system is impaired in its ability to respond to the therapeutic virus but continues to attack the tumor, thus enhancing the therapy dramatically, leading to a 60-80% durable cure rate in a very challenging cancer model. This represents the first time that anti-melanoma efficacy was dramatically enhanced with a simultaneous and equally dramatic reduction in vitiligo.

In summary, an oncolytic vaccine therapy was combined with an HDACi to impair innate immunity and mediate significant modification of both anti-viral and anti-tumoral acquired immunity. By delaying anti-viral responses while focusing the immune response on the tumor, viral oncolysis was extended, anti-tumor efficacy was enhanced and autoimmune sequelae were reduced.

All references referred to herein are incorporated by reference.

We claim:

1. A method of enhancing immune response in a mammal to an antigen to which the mammal has a pre-existing immunity that results from immunization of the mammal with the antigen comprising co-administering to the mammal a histone deacetylase inhibitor and a viral vaccine comprising an oncolytic recombinant vesicular stomatitis virus or Maraba virus that expresses the antigen, wherein administration of the histone deacetylase inhibitor and the viral vaccine results in at least about a 2-fold increase in the mammal's immune response to the antigen in comparison to the immune response to the antigen induced by the viral vaccine alone.

2. The method of claim 1, wherein the antigen is selected from the group consisting of tumour antigens, antigens from viral pathogens and antigens from bacterial pathogens.

3. The method of claim 2, wherein the tumour antigen is selected from the group consisting of alphafetoprotein (AFP), carcinoembryonic antigen (CEA), cancer antigen 125 (CA 125), Her2, dopachrome tautomerase (DCT), GP100, MART1, Melanoma Antigen Gene (MAGE) protein, NY-ESO1, human papillomavirus (HPV) E6 and HPV E7.

4. The method of claim 1, wherein the antigen is from a pathogenic organism selected from the group consisting of human immunodeficiency virus (HIV), hepatitis C virus (HCV), feline immunodeficiency virus (FIV), Lymphocytic choriomeningitis (LCMV), Ebola virus and mycobacterium tuberculosis.

5. The method of claim 1, wherein the histone deacetylase inhibitor is selected from the group consisting of hydroxamic, benzamides, cyclic tetrapeptides, depsipeptides, electrophilic ketones, and aliphatic acid compounds.

6. The method of claim 5, wherein the hydroxamic acids are selected from vorinostat (SAHA), belinostat (PXD101), LAQ824, trichostatin A and panobinostat (LBH589); the benzamides are selected from entinostat (MS-275), CI994 and mocetinostat (MGCD0103); the cyclic tetrapeptide is trapoxin B); and the aliphatic acid compounds may be phenylbutyrate or valproic acid.

7. The method of claim 1, wherein the vaccine induces expression of type I interferon.

8. The method of claim 1, wherein the vaccine is administered in combination with an agent that induces expression of type I interferon.

9. A composition for enhancing immune response in a mammal to an antigen to which the mammal has a pre-existing immunity comprising a viral vaccine that expresses the antigen and a histone deacetylase inhibitor, wherein the viral vaccine is an oncolytic recombinant vesicular stomatitis virus or Maraba virus that expresses the antigen.

10. The composition of claim 9, wherein the vaccine induces type I interferon.

11. The composition of claim 9, wherein the histone deacetylase inhibitor is selected from the group consisting of hydroxamic, benzamides, cyclic tetrapeptides, depsipeptides, electrophilic ketones, and aliphatic acid compounds.

12. The composition of claim 11, wherein the hydroxamic acids are selected from vorinostat (SAHA), belinostat (PXD101), LAQ824, trichostatin A and panobinostat (LBH589); the benzamides are selected from entinostat (MS-275), CI994 and mocetinostat (MGCD0103); the cyclic tetrapeptide is trapoxin B); and the aliphatic acid compounds may be phenylbutyrate or valproic acid.

13. The composition of claim 9, additionally comprising an agent that induces expression of type I interferon.

14. The composition of claim 13, wherein the agent is selected from the group consisting of toll-like receptor ligand, imiquimod, polyinosine-polycytidylic acid (polyI:C), CpG ODN, imidazquinoline, momophosphoryl lipid A, flagellin, FimH and N-glycolyted muramyldipeptide.

15. The composition of claim 9, wherein the antiigen is a tumour antigen.

16. The composition as defined in claim 15, wherein the tumour antigen is selected from the group consisting of alphafetoprotein (AFP), carcinoembryonic antigen (CEA), CA 125, Her2, dopachrome tautomerase (DCT), GP100, MART1, MAGE protein, NY-ESO1, HPV E6 and HPV EV7.

17. The method of claim 1, which the vaccine is administered intravenously.

* * * * *

UNITED STATES PATENT AND TRADEMARK OFFICE
CERTIFICATE OF CORRECTION

PATENT NO. : 9,821,054 B2  
APPLICATION NO. : 14/004546  
DATED : November 21, 2017  
INVENTOR(S) : Byram Bridle et al.

Page 1 of 1

It is certified that error appears in the above-identified patent and that said Letters Patent is hereby corrected as shown below:

In the Claims

At Column 12, Line 54, "hydroxamic," should read --hydroxamic acids,--; and  
At Column 13, Line 11, "hydroxamic," should read --hydroxamic acids,--.

Signed and Sealed this  
Seventeenth Day of April, 2018

Andrei Iancu  
*Director of the United States Patent and Trademark Office*